United States Patent [19]

Wixon et al.

[11] Patent Number: 5,624,444
[45] Date of Patent: Apr. 29, 1997

[54] FEMORAL RESECTION INSTRUMENTATION INCLUDING THREE-DIMENSIONAL JIG AND METHOD OF USE

[76] Inventors: Richard Wixon, 55 W. Goethe St. #1224, Chicago, Ill. 60610; Christine Chernesky, 626 Third Ave., Lyndhurst, N.J. 07071

[21] Appl. No.: 386,405

[22] Filed: Feb. 10, 1995

[51] Int. Cl.$^6$ .................... A61B 17/15; A61B 17/17
[52] U.S. Cl. ........................................ 606/88; 606/96
[58] Field of Search ............................ 606/79, 82, 86, 606/87, 88, 89, 96, 97, 98

[56] References Cited

U.S. PATENT DOCUMENTS

| | | |
|---|---|---|
| 4,474,177 | 10/1984 | Whiteside . |
| 4,567,885 | 2/1986 | Androphy . |
| 4,722,330 | 2/1988 | Russell et al. . |
| 4,759,350 | 7/1988 | Dunn et al. . |
| 5,035,700 | 7/1991 | Kenna . |
| 5,037,423 | 8/1991 | Kenna . |
| 5,053,037 | 10/1991 | Lackey . |
| 5,100,408 | 3/1992 | Lackey . |
| 5,122,144 | 6/1992 | Bert et al. . |
| 5,250,050 | 10/1993 | Poggie et al. . |
| 5,282,803 | 2/1994 | Lackey . |
| 5,454,816 | 10/1995 | Ashby ........................... 606/88 |

OTHER PUBLICATIONS

"Osteonics Series 7000 Total Knee System Surgical Protocol For The A.R. Instruments" Brochure pp. 1–31.

*Primary Examiner*—Gary Jackson
*Assistant Examiner*—Scott B. Markow
*Attorney, Agent, or Firm*—Pennie & Edmonds

[57] ABSTRACT

A set of instruments and method for use in knee replacement surgery, specifically to make the necessary femoral resections is described. The simplified set of instruments allows the necessary femoral resections to be performed with fewer instruments, and with fewer necessary steps for the surgeon to take. The set of instruments includes a three-dimensional jig which references the anterior and posterior femoral condyles to allow determinations as to alignment, placement, and prosthesis size before any bone cuts are made.

14 Claims, 6 Drawing Sheets

5,624,444

FEMORAL RESECTION INSTRUMENTATION INCLUDING THREE-DIMENSIONAL JIG AND METHOD OF USE

BACKGROUND

The present invention relates to surgical instrument systems for performing knee surgery in general, and more particularly to instrument systems for making the necessary distal femoral resections.

Replacement knee surgery has become increasingly common over the last several years, leading to the development of increasingly sophisticated instruments for making the required resections of the femur and tibia. There are three basic resections of the distal femur that must be made: the distal femoral condyles; the anterior femoral condyles; and the posterior femoral condyles. These resections must be made accurately to ensure that the femoral component of the knee prosthesis will fit securely onto the femur.

Prior art knee instrumentation systems often require surgeons to make several cuts in order to make the same resection of the distal femur. Repeated cuts are necessary because the prior art instruments require that an initial cut be made in order to determine the proper alignment, corresponding depth of related cuts, and the size of the appropriate femoral prosthesis. For example, U.S. Pat. No. 4,759,350 to Dunn et al. describes a set of instruments for shaping distal femoral surfaces in which a second cut of the anterior femoral condyle is required to create the proper angle for receiving the femoral component, and the size of the femoral component is not determined until after the anterior and distal femur have been resected.

SUMMARY OF INVENTION

The object of the present invention is to provide a system of instruments and method of use that allows for a simplified surgical technique for making the necessary distal femoral cuts for knee replacement surgery.

Specifically, it is an object of the present invention to allow the surgeon to make all decisions relating to implant size, alignment, and placement before any cuts are made. It is a further object of the invention to make a single angled anterior cut, instead of requiring a second "clean-up" cut as is done in the prior art.

In addition, it is an object of the present invention to allow a surgeon to control the resection amounts in increments before cuts are made, to compensate for knees that measure between existing sizes.

The instruments of the present invention have been designed to reference the anterior cortex of the femur by using a three-dimensional jigging system which designates the amount of bone to be resected distally and posteriorly. By using this system, the goals of shaping the bone and obtaining full range of motion with good kinetics can be achieved. The system allows for controlled adjustments of resected distal and posterior bone in two and four millimeter increments. This "controlled resection" technique is unique when compared with prior art systems. This feature will prevent notching of the anterior cortex or the condition of having too proud an anterior flange.

The system also incorporates a femoral intramedullary alignment system which allows one degree increments of selection for planning the amount of valgus angle needed. In addition, compensation for external rotation can be obtained by the use of spacer removably located on the posterior skids of the jig. Therefore, both the valgus angle and external rotation can be adjusted before cuts are made, which is also unique when compared to prior art systems.

Decisions on implant size, alignment, and placement are all interconnected. With this system the valgus angle and external rotation are established, the depth of the anterior cortical cut is determined, the size of the prosthesis is selected, the depth of the distal femoral cut is marked, and the amount of bone to be resected posteriorly for that size implant is known prior to any cuts being made. The initial cut is an angled anterior cut which is parallel to the angle of the anterior flange of the prosthesis. The ability to make this angled cut does away with the need to make a second clean-up anterior cut which is a feature on other prior art systems.

These and other objects are achieved with a set of instruments comprising a three-dimensional jig having a body portion with parallel distal and proximal base faces, and posterior and anterior base faces, further including a posterior portion, slideably engaged with the body portion and cooperating with a sizing indicator on the distal face of the body portion. The posterior portion includes two skids extending in the proximal direction from the body portion, which are adapted to contact the posterior femoral condyles. The body portion of the jig also has an aperture for receiving an intramedullary ("IM") bushing. The IM bushing is adapted to receive an intramedullary ("IM") rod, and the IM bushing further includes a valgus angle guide adapted to position an intramedullary rod within the range of 15 degrees below and 15 degrees above an angle of ninety degrees with the distal face of the body portion of the jig.

The set of instruments also includes a stylus removably attached to the anterior face of the body portion of the jig. The stylus includes a cross bar which is slideably engaged with the stylus and cooperates with a sizing indicator on the stylus. The cross bar extends in the proximal direction, and at its proximal end has a nose portion which is placed in contact with the anterior cortex.

In addition, a distal cutting guide is provided that is removably attached to the anterior face of said body portion, and provides a plurality of fixation holes and a slot for guiding a resection of the distal femur. Fixation holes are provided in at least two millimeter increments to allow for alteration of sizes.

The anterior surface of said jig is adapted to create an angular surface equal to the angular surface required by the femoral prosthesis to be implanted, and in use with a femoral prosthesis that requires an obtuse angle to be formed by the distal cut and the anterior cut, the same angle will be incorporated by the proximal face of the jig and the distal cutting block.

The set of instruments further includes a spacer adapted to fit on the proximal surface of one of said skids of said jig, which allows a surgeon to compensate for external rotation.

The set of instruments can also include a pin holder alignment guide, which fits on the femur after the anterior and distal cuts are made, and allows for placement of pins into the distal end of the femur through apertures in the alignment guide corresponding to the desired size of the prosthesis. Holes are drilled into the femur corresponding to the apertures of the alignment guide, which are used in conjunction with a chamfer cutting guide, which contains two extending pin portions which fit into the holes of the femur. The chamfer cutting guide is provided with slots to guide a saw blade to make the posterior resection and the chamfer cuts.

Alternatively, a substantially L-shaped custom chamfer cutting guide that fits against the cut anterior and distal surfaces can be used, which does not require the pin locator block. The custom chamfer cutting guide of the appropriate size is placed on the femur, fixed with fixation pins, and then slots for each chamfer cut and the posterior cut are used to guide a saw blade.

The present invention also includes the method for performing the necessary femoral resections, which comprises the steps of drilling a hole in the IM canal of the femur, and providing the equipment described above for use in the surgical technique.

The surgical technique of performing the three basic resections with the equipment involves the steps of: (1) setting the IM bushing to the desired valgus angle; (2) attaching the stylus to the anterior surface of the jig; (3) flexing the knee to greater than 90°; (4) inserting an IM rod through the IM bushing and into the femur; (5) placing the skids against the posterior condyles of the femur; (6) positioning the jig against the uncut distal femoral condyle; (7) noting the size indicated on the distal face of the jig; (8) positioning the stylus to the same size; (9) fixing the jig to the bone through the oblique holes located on the side of said jig; (10) removing the stylus from the jig; (11) making the anterior cut; (12) attaching the distal cutting block; (13) placing fixation pins in the most proximal holes of the block and then adjusting in 2 or 4 millimeter increments according to the proper size; (14) removing the jig; (15) assessing implant size; (16) making the distal cut using the slot provided on the distal cutting block; and (17) making the posterior and chamfer cuts using a chamfer cutting guide. Additional steps are also described herein for situations in which a patient might have more specialized needs.

DETAILED DESCRIPTION

Figure 22:
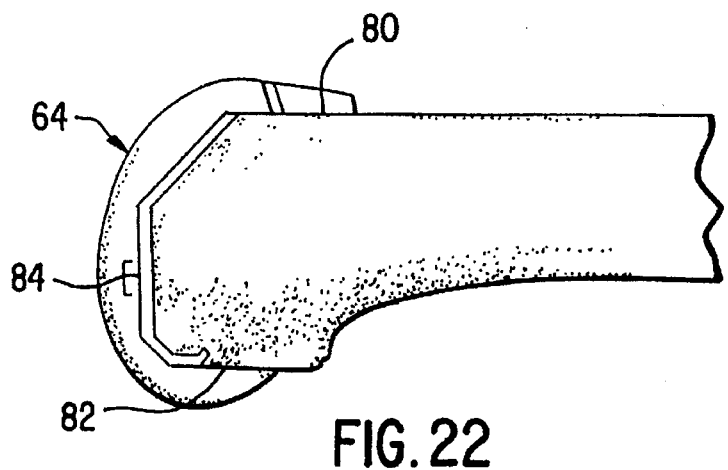
FIG. 22 is a side elevation view of a trial femoral component on the cut femur.

The surgical technique using the instruments and method of the present invention highlights the beneficial features of the instruments. The instruments of the present invention allow the distal femoral resections to be performed in an efficient manner, requiring fewer steps and instruments, and yet allowing greater flexibility to adapt the cuts to a particular patient's needs. The cuts are made in order to affix a femoral component to the femur. A femoral component is shown in FIG. 22, with the anterior cut 80, posterior cut 82, and distal cut 84 shown. Additional angled chamfer cuts are also required, which will be described herein.

Figure 1:
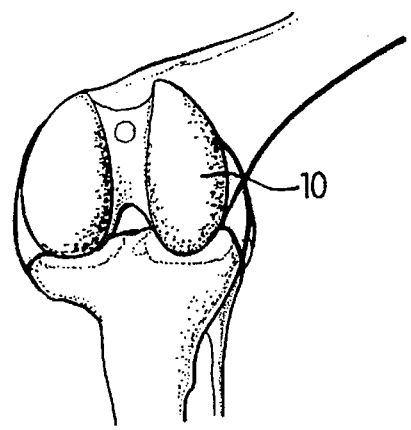
FIG. 1 is a perspective view of an exposed femur with an open intramedullary canal.

The first step in using the instruments, as shown in FIG. 1, is to expose the knee and use a drill (preferably 5/16") to open the intramedullary ("IM") canal of the femur 10, as is well known in the art.

Figure 2:
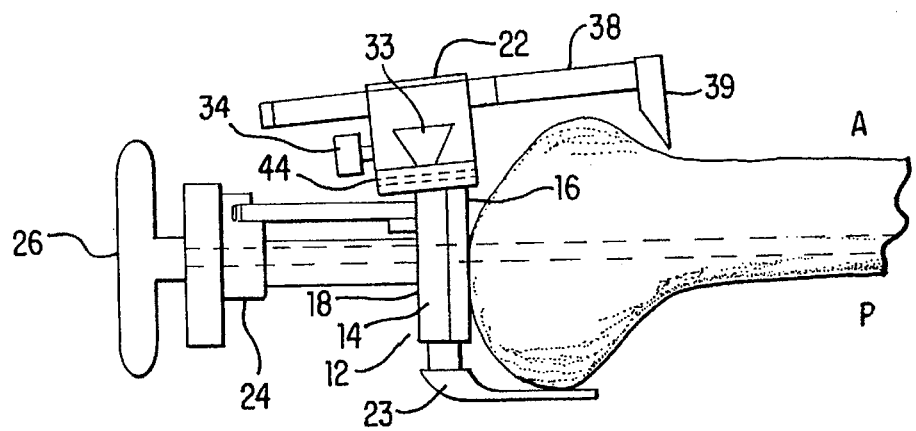
FIG. 2 is side elevation view of the jig, with the IM rod, IM bushing, and stylus attached to the femur.
Figure 3:
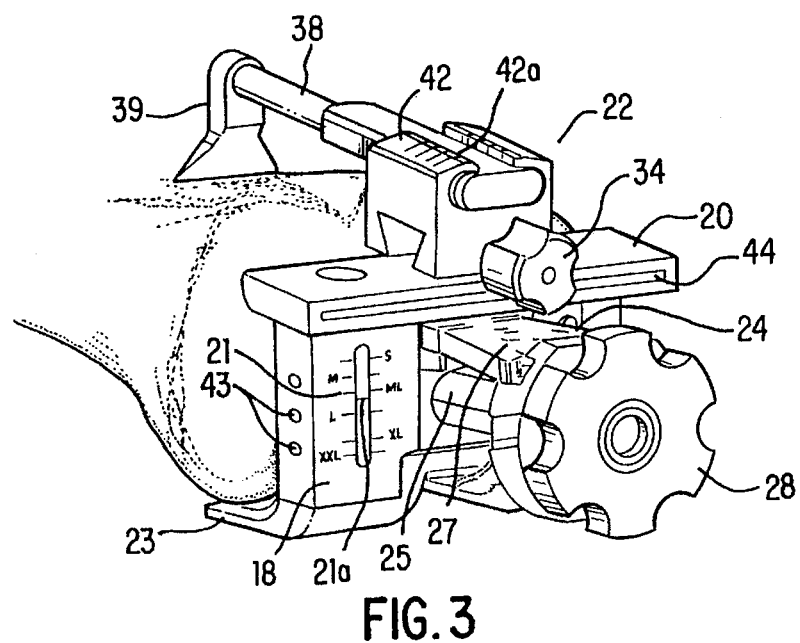
FIG. 3 is a perspective view of the jig, with the IM bushing and stylus attached to the femur.

Next, the jig 12 is prepared and placed on the femur. The jig 12 is shown in a side view in FIG. 2, and in a perspective view in FIG. 3. As shown in FIGS. 2 and 3, the jig 12 has a body portion 14 with a proximal face 16 and a distal face 18. In addition, the body portion has a anterior face 20, onto which the stylus 22 is removably attached. The posterior portion of jig 12 comprises two curved portions or "skids" 23 which extend proximally and in use rest against the posterior femoral condyles. The skids 23 are mounted on pins that are slideably engaged with the body portion 14 to allow adjustment in the anterior/posterior directions for different size femurs. The position of the skids 23 is indicated by the sizing guide 21 located on the distal face 18 of the jig, which is calibrated with an indicator 21a on the pins on which the skids 23 are mounted. The jig 12 also attaches to an IM bushing 24, which allows the jig 12 to be positioned using an IM rod 26. The use of an IM rod 26, a generally cylindrical rod with the proximal end inserted into the femoral intramedullary canal and with a handle at the distal end, is generally known in the art.

Figure 4:
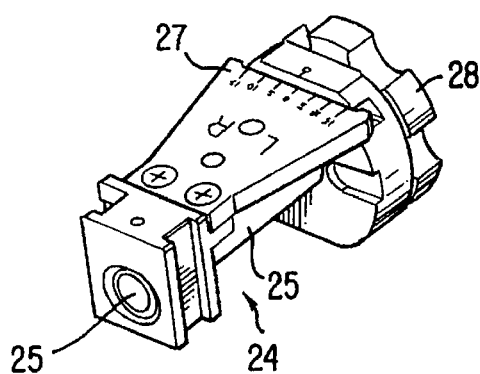
FIG. 4 is a perspective view of the IM bushing of FIGS. 2 and 3.

The IM bushing 24 is shown in FIGS. 3 and 4, and has a tubular portion 25, through which the IM rod 26 slides, a valgus guide 27, and a knob 28. The knob 28 is preferably spring loaded so that the knob 28 can be pulled away from the jig 12, moved to the right or left to the desired angle indicated on the valgus guide 27, and then released, allowing a spring to hold the tubular portion 25 at the desired angle.

Figure 5:
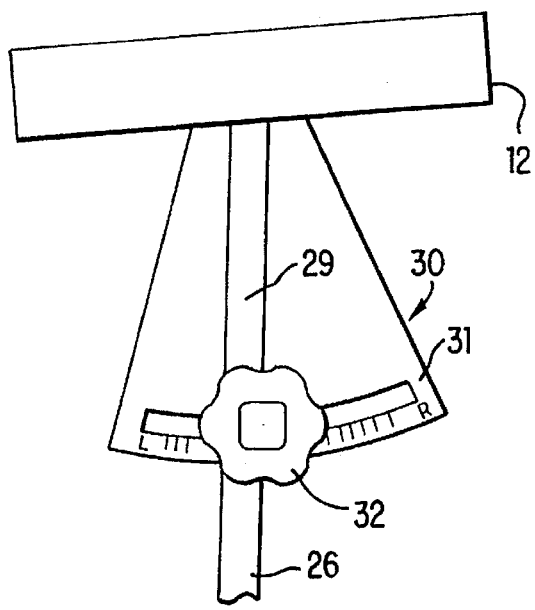
FIG. 5 is a top plan view of an alternative embodiment of the IM bushing attached to the jig.

An alternative embodiment is shown in FIG. 5, in which the IM bushing 30 has a tubular portion 29 through which the IM rod 26 slides. In addition, the bushing 30 has a valgus guide 31, which the tubular portion 29 slides relative to, allowing the entire jig 12 to be positioned relative to the valgus angle of a particular patient, as is discussed further below.

Preparation of the jig involves first, setting the IM bushing 24 or 30 to the desired degree of valgus angle using the valgus guide 27 or 31. The tubular portions 25 and 29 are pivotally mounted on their respective bushings 24 and 30, using mounting pins. As shown in FIGS. 4 and 5, the valgus guide 27 or 31 has demarcations for various degrees of valgus angle. The surgeon may adjust the tubular portion 25 or 29 by moving it to the appropriate, predetermined valgus angle for the particular patient. The valgus angle guide 27 or 31 remains stationary as the tubular portion 25 or 29 is pivoted from side to side. In the IM bushing of FIG. 4, a spring preferably holds the tubular portion 25 at the desired angle. In the alternative embodiment of FIG. 5, a locking mechanism, for example a tightening screw 32 is provided to secure the particular angle for the resections.

Once the valgus angle is set, the stylus 22 is attached to the anterior surface 20 of the jig 12, as shown in FIGS. 2 and 3. The means for attaching and locking the stylus 22 to the jig 12 are preferably a "dovetail" arrangement in which the stylus 22 has a "dovetail" shaped opening which mates with an extending portion 33 of the body portion 14 of the jig. A knob 34 which turns an internal tightening screw is further provided to secure the stylus 22 to the extending portion 33. The means for attaching could alternatively be a screw with a knob extending from the anterior surface of the stylus 22 which mates with a hole in the anterior surface 20 of the jig 12, which would not require a "dovetail" arrangement. Any type of locking mechanism which is secure and easy to use during surgery could be adapted for attaching the stylus 22.

Figure 6:
FIG. 6 is a side elevation of an external rotation spacer.
Figure 7:
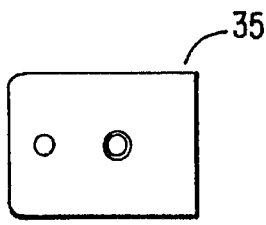
FIG. 7 is a plan view of a spacer.
Figure 8:
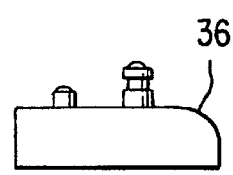
FIG. 8 is a side elevation view of a posterior revision spacer.

The surgeon may then assess the need for compensation due to external rotation, which varies from patient to patient. If indicated, the surgeon can then attach a 3° external rotation spacer 35 to the anterior surface of the appropriate skid 23, as illustrated in FIGS. 6 and 7. In order to compensate for three degrees of external rotation, the spacer 35 is preferably approximately 0.1 inch in thickness, or most preferably 0.103 inch. The spacer 35 is provided with means for removably attaching the spacer to the skids 23, preferably in the form of protruding cylindrical members, shown in FIG. 6. The protruding members snap-fit with openings on the skids 23 (not shown). Alternatively, threaded members or any secure attachment means could be used.

Similarly designed spacers are also used for revision purposes. FIGS. 7–11 also illustrate the two types of spacers used for revision surgery. The use of the revision spacers, which occurs when a patient needs femoral and tibial components of differing sizes, is further described below. The revision spacers are of two types, posterior revision spacers and distal revision spacers. The external rotation spacer 35 is the same design as the posterior revision spacers 36, which are also adapted to fit on the anterior side of the skids 23, and contact the posterior femur. The posterior revision spacer usually differs in that it is of a greater thickness. The posterior revision spacer 36 is generally nine millimeters in thickness, or approximately 0.354 inch.

Figure 9:
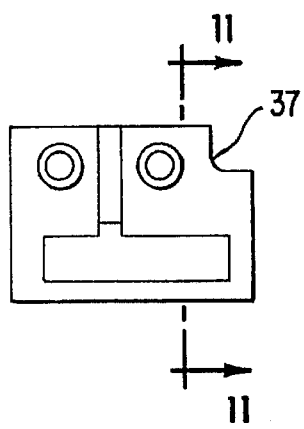
FIG. 9 is a plan view of a distal revision spacer.
Figure 10:
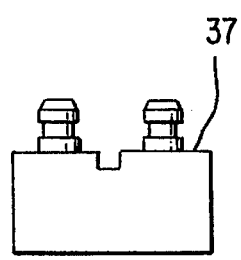
FIG. 10 is a side elevation view of the spacer of FIG. 9.
Figure 11:
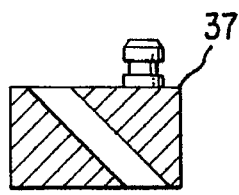
FIG. 11 is a cross-sectional view along line 11—11 of FIG. 9.

There are also provided two distal revision spacers 37, shown in FIGS. 9–11. The distal revision spacers 37 are placed on the proximal face 16 of the jig 12, using similar attachment means as described above. The distal revision spacers 37 are further provided with an angled slot to allow fixation pins placed in the oblique holes 43 of the jig to access the femur, as shown in FIG. 11.

Once the jig is prepared, the knee is flexed to greater than 90° and the IM rod 26 is inserted through the tubular portion of the IM bushing 24, and into the IM canal of the femur 10. At this point the skids 23 should be positioned so that they are both in contact with the posterior femoral condyles. Screws, which could, for example, be located on the anterior face 20 or sides of the jig, are used to set the skids 23 into the desired position. The position of the skids 23 will also indicate a size by the position of the indicator 21a on the sizing guide 21 located on the distal face of the jig. The proximal face of the jig 12 is then positioned against the uncut distal femoral condyle, as shown in FIGS. 2 and 3.

The next step is to determine the anterior cut and the implant size. This step involves the use of the stylus 22. The stylus 22 is attached to the anterior face 20 of the jig 12 at its distal end as described above. The stylus 22 further comprises a cross bar 38 which is slideably engaged at the distal end. The proximal end of the cross bar 38 has a nose 39 that contacts the anterior cortex of the femur. The distal end of the stylus also has a sizing guide 42 which has markings that act in cooperation with an indicator on the cross bar 38, which together are calibrated to indicate a particular size.

With the jig 12 flush against the distal condyle, the stylus 22 is slid proximally until the cross bar 38 contacts the distal anterior cortex of the femur. This position indicates the intersection of the anterior cut and the cortex of the femur. The cross bar 38 is adjusted so that an indicator 42a on the cross bar indicates a size on the sizing guide 42 of the stylus 22, which matches the size indicated on sizing guide 21 on the jig 12. Once the sizing guide 42 is set to the appropriate size, the location of the nose 39 at the proximal end of the cross bar 38, is where the proximal end of the anterior cut will be when it is later made. The use of the stylus 22 allows the surgeon to determine the location of the anterior cut for the size determined by the sizing guide 42 of the jig, before making the actual resection. The stylus 22 therefore prevents notching of the bone or too proud a flange, and allows a surgeon to reassess the implant size before making any bone resections if one of these conditions occurs.

The jig 12 is then fixed to the bone with pins (preferably ⅛") placed through the oblique holes 43 located on the sides of the jig 12.

Figure 12:
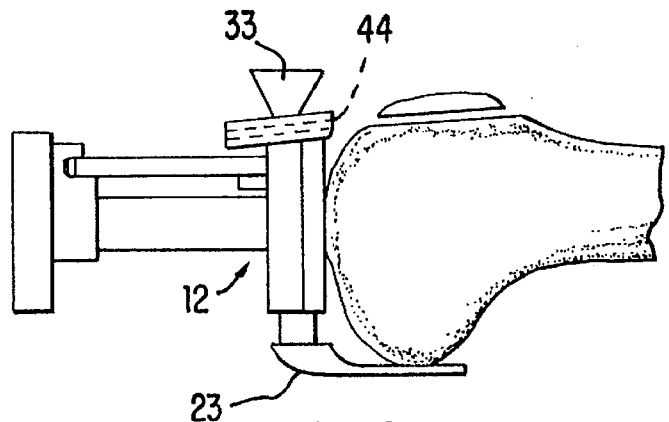
FIG. 12 is a side elevation view of the jig positioned to make the anterior cut.

The next step involves making the anterior cut. First, the stylus 22 is removed from the jig 12. The surgeon may then use the anterior slot 44 of the jig 12 as a cutting guide, and cut the anterior femoral condyles using a conventional saw, as shown in FIG. 12. Alternatively, an anterior slot 44 is not provided, and the anterior surface 20 of the jig 12 can be used as a cutting guide. If an anterior slot is used, it is designed to be parallel to the anterior surface 20, which is in turn designed to be parallel to anterior flange of the prosthesis 64 (of FIG. 22) to be affixed to the femur. (Shown in FIG. 22 as 80.) Therefore, a second clean-up cut is not required to match the angle of the prosthesis.

Figure 13:
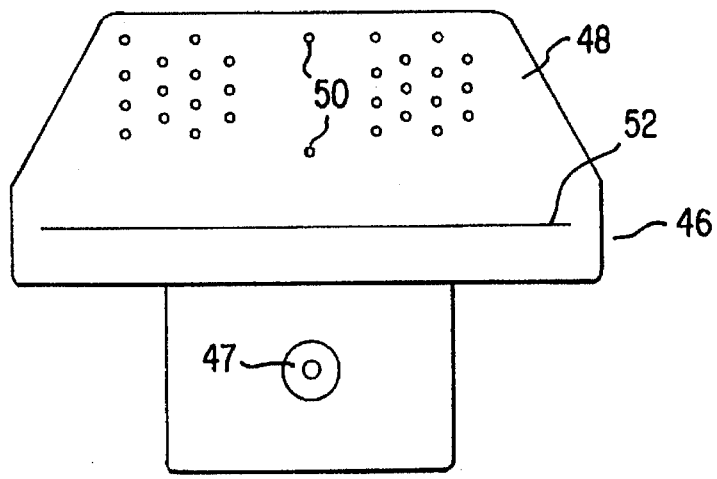
FIG. 13 is a plan view of the distal cutting block.

The next step is to make the distal cut. The distal cutting block 46 is attached to the anterior surface of the jig 12. Preferably, the distal cutting block 46 slides in a lateral/medial direction onto the extending portion 33 of the jig 12. The distal cutting block 46 has a female opening which mates with the extending portion 33 in the medial/lateral direction. A tightening screw 47 is further provided to secure the block to the jig 12. The distal cutting block 46 contains a plurality of fixation holes 48 at different locations shown in FIG. 13. The different fixation holes 48 allow for various size prosthesis to be accommodated.

Figure 14:
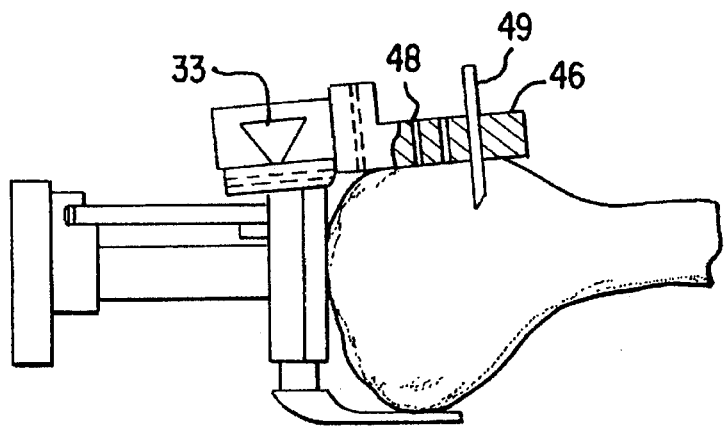
FIG. 14 is a side elevation view of the jig and distal cutting block of FIG. 13 attached.
Figure 15:
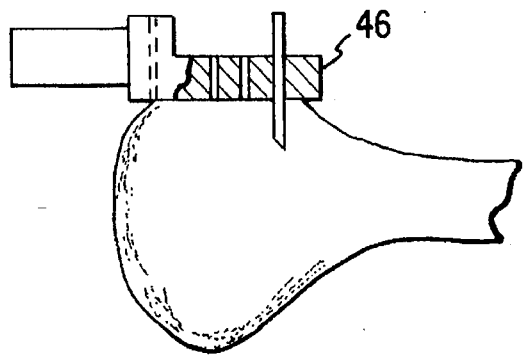
FIG. 15 is a side elevation view of the distal cutting block with a fixation pin inserted into the most proximal fixation opening.

In the normal case, pins 49 (preferably ⅛") are placed in fixation holes designated for standard resections, into the femur, as shown in FIG. 14, affixing the distal cutting block 46 onto the femur. The jig 12 is then unscrewed and removed, as shown in FIG. 15. At this point the implant size should be assessed. The distal cutting block 46 will remove ten millimeters of bone as measured from the contact point of the jig 12 with the distal condyle of the femur. If the size indicated on the sizing guide 21 of the jig 12 was close to or an exact match with one of the sizes, ten millimeters resection is appropriate. Ten millimeters of bone will also be removed from the posterior condyles when that cut is made. This results in balanced flexion and extension gaps.

Figure 16:
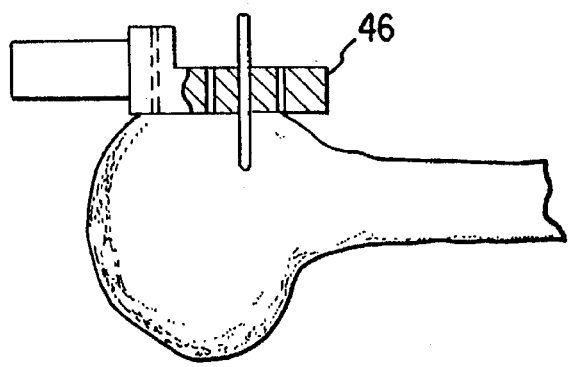
FIG. 16 is a side elevation view of the distal cutting block with a fixation pin after adjusting a 2 millimeter increment.

However, when the sizing guide 21 is halfway between sizes, the system is designed to use the smaller of the two sizes. With the distal cutting block 46 in its standard position, the distal cut will remove ten millimeters of bone from the distal end of the femur. However, because a smaller size prosthesis is being used, an additional two millimeters of bone will be later removed from the posterior condyles. This could potentially lead to a knee which is normal in extension but potentially more lax in flexion. To compensate for this, the distal cutting guide 46 can be shifted two millimeters proximally to a different fixation hole, which allows an additional 2 mm of distal bone to be resected, as shown in FIG. 16. This will assure proper balance of the flexion and extension gaps. This adjustment can be made at this point in the surgery on the basis of experience or clinical judgment. However, due to the ease in which the distal femur can be recut it is often preferable to wait until the knee is further balanced by soft tissue release and osteophyte removal before removing additional distal bone.

Figure 17:
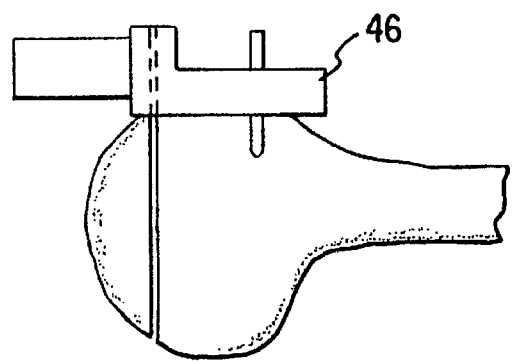
FIG. 17 is a side elevation view of the distal femoral cut being made using the distal cutting jig.

Once the correct size has been determined, the distal cutting block 46 is fixed to the bone by placing ⅛" pins through the oblique holes 50 (shown in FIG. 13) on the block 46. A slot 52 is then used as a guide to make the distal cut using conventional saw means, as shown in FIG. 17. The distal cutting block 46 is then removed.

Figure 18:
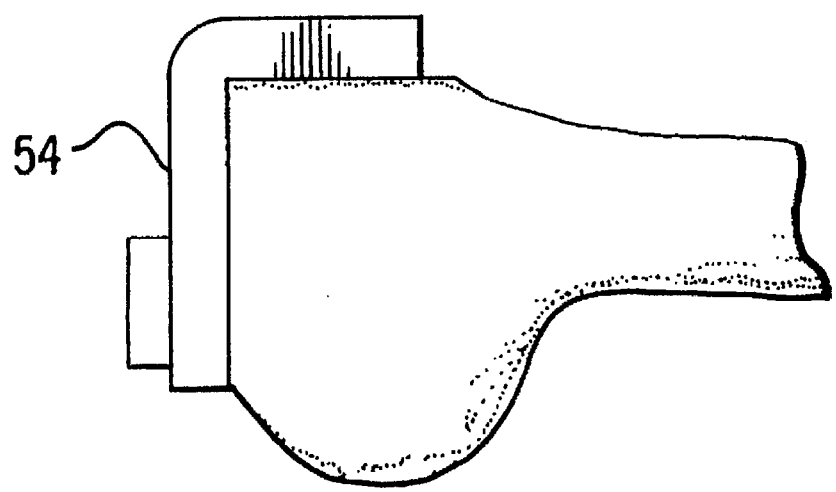
FIG. 18 is a side elevation view of the pin locator block placed on the distal femur.
Figure 19:
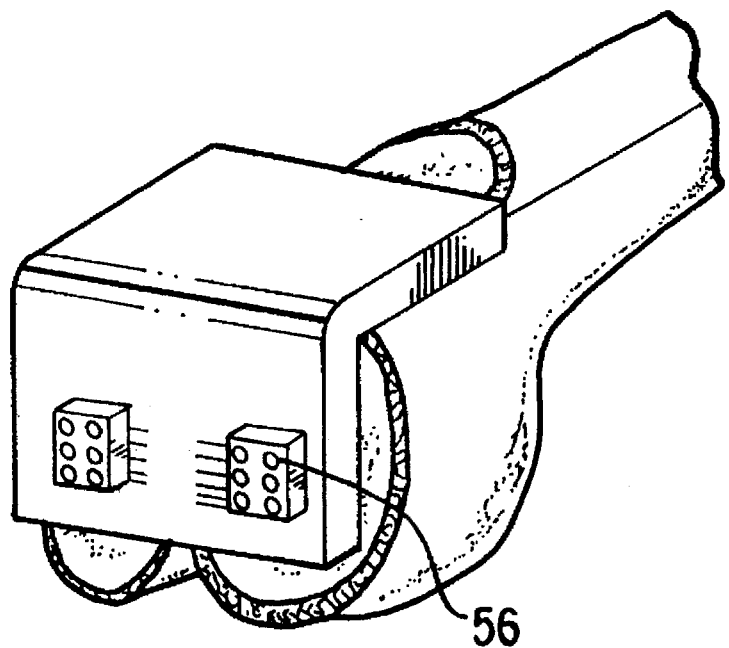
FIG. 19 is a perspective view of the pin-locator block on the distal femur.

In order to make the remaining cuts to prepare the femur, the pin locator block 54 is placed on the femur, as shown in FIGS. 18 and 19. The surgeon then visually inspects the fit of the block 54 to ensure it contacts the anterior and distal surfaces without any gaps medially or laterally. The pin locator block 54 references the anterior and distal cut to locate two pin holes which correspond to designated sizes for the prosthesis. Pairs of apertures 56 are provided on the pin locator block 54 which correspond to various sizes, as shown in FIG. 19. Once the apertures of the desired size are selected, they are marked on the distal end of the femur, and a 3/16" drill is used to open the holes.

Figure 20:
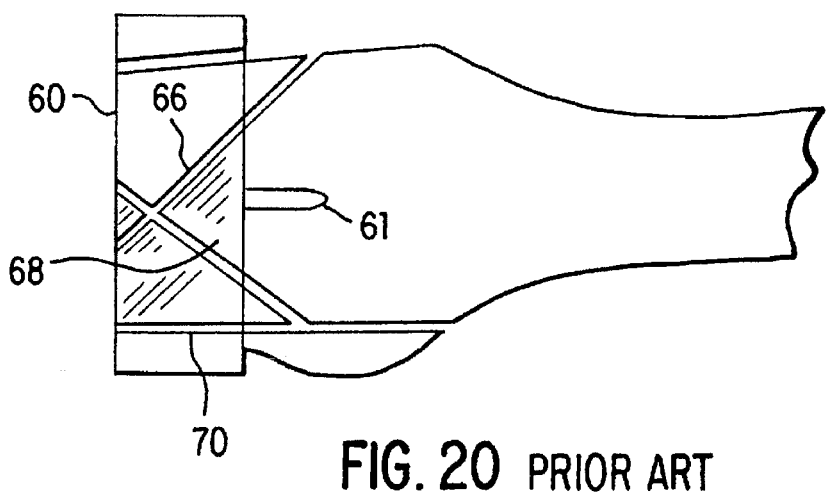
FIG. 20 is a side elevation view of a standard chamfer cutting guide on the distal femur.

The remaining cuts are the posterior resection and the two chamfer cuts. As shown in FIG. 20, a conventional chamfer cutting guide 60, which is substantially rectangular in shape, is placed on the distal femur and the remaining cuts are completed. Chamfer cutting guides 60 come in a variety of sizes, a particular size is chosen by the surgeon to correspond with the size previously established by the sizing guide 21 of the jig. Each chamfer cutting guide 60 has two extending pin portions 61 which fit into the holes of the femur positioned by the pin locator block 54. When the extending portions 61 of the chamfer cutting guide 60 are inserted into the drilled holes, the chamfer cutting guide 60 will be in the proper position to make the posterior and chamfer cuts for the chosen size.

In order to guide the saw blade, the cutting guide 60 is provided with three elongated rectangular apertures or slots that extend between the top surface of the cutting guide 60 which is placed against the flat-cut distal femur, and the bottom surface of the cutting guide (the distal side). For the chamfer cuts, two angled apertures are provided. The first aperture 66 and second aperture 68 extend between the top and bottom surfaces, each forming an acute angle with the top surface, with the acute angles facing each other, located near the center of the cutting guide 60. For the posterior cut, an elongated aperture 70 is provided which is located near the posterior end of the cutting guide 60.

Figure 21:
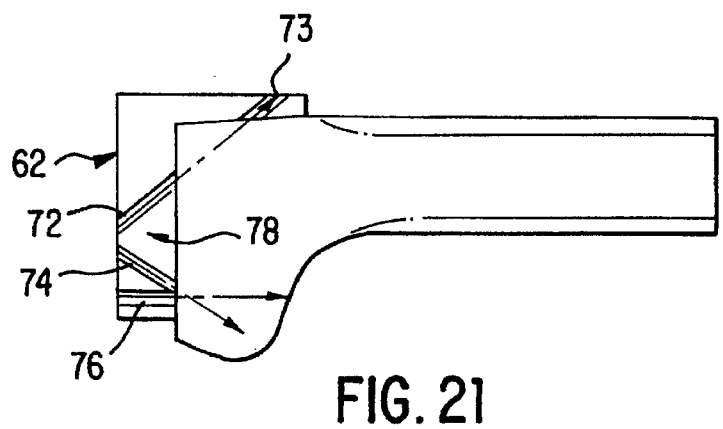
FIG. 21 is a side elevation view of a custom chamfer cutting guide on the distal femur.

Alternatively, as shown in FIG. 21, a substantially L-shaped custom chamfer cutting guide 62, specially designed for the claimed set of instruments, could also be used. The custom chamfer cutting guide 62 has a anterior portion which contacts the anterior cut surface of the femur, and a distal portion with a top surface that contacts the distal cut surface of the femur. The cutting guide 62 uses the distal and anterior cuts as reference points, and does not therefore require the use of the pin locator block 54. The custom chamfer cutting guide 62 is provided in a variety of sizes, allowing a surgeon to use the chamfer cutting guide of the appropriate size as determined earlier. Due to the fact that the chamfer cutting guide 62 is placed in relation to the anterior resection, which has already been made, the custom chamfer cutting guide 62 incorporates an angle of slightly greater than 90° between the anterior portion and the distal portion.

The cutting guide 62 is also provided with oblique holes 78, with at least one hole on each side of the cutting guide. Fixation pins are placed through the holes 78 to contact the femur and fix the cutting guide in place before using a saw blade to make the cuts.

The custom chamfer cutting guide 62 is also provided with a plurality of elongated apertures to guide a saw blade to make the chamfer cuts and posterior cut. For the anterior chamfer cut, two apertures are provided. The first aperture 72 extends through the distal portion of the cutting guide 62 to form an acute angle with the top surface facing the center of the cutting guide. The second aperture 73 extends through the anterior portion of the cutting guide in the same plane as the first aperture 72, so as to allow a saw blade to pass through both apertures 72 and 73 to make the anterior chamfer cut. For the posterior chamfer cut, an aperture 74 is provided that extends through the distal portion of the cutting guide 62 and forms an acute angle with the top surface, with the angle facing the angle formed by aperture 72 with the top surface. A fourth aperture 76 is provided to guide the saw blade to make the posterior cut.

After the cuts, the chamfer cutting guide 60 or 62 is removed, and a trial implant 64 can be placed on the femur to verify the accuracy of the cuts, as shown in FIG. 22.

In certain situations, the above procedure is modified due to patient anatomy, sizing or unusual circumstances in which the femoral component must be downsized to avoid a significant overhang of the tibial component. Downsizing generally requires resecting two millimeters of additional bone from each of the three basic cuts. In this situation, the revision spacers 36, 37 shown in FIGS. 7–11 are necessary. If the bone will allow it without significant notching, the jig 12 can be re-applied to the femur using the IM rod for alignment. The posterior revision spacer 36 may be placed on the skids 23, and the distal revision spacers 37 may be placed on the proximal face 16 of the jig 12. These spacers 36, 37 compensate for the bone that has previously been resected. The distal cutting guide 46 can then be used as described above to take two millimeters off the distal femur. A chamfer cutting guide of the next smaller size can then be used to take two millimeters off the anterior and posterior femoral condyles, and reshape the chamfer cuts. The additional cuts will allow a femoral component of the next smaller size to then be used.

We claim:

1. A set of instruments for use in the preparation of the distal end of a femur for the implantation of a femoral prosthesis, which implantation requires resecting the anterior femoral condyles by making an anterior cut, distal femoral condyles by making a distal cut and first and second angle cuts, and posterior femoral condyles by making a posterior cut, said set comprising:

a jig comprising a body portion having parallel distal and proximal base faces, connected by parallel posterior and anterior base faces, wherein the proximal base face is adapted to abut the distal end of the femur;

said jig further including a posterior portion slideably engaged with said body portion for movement parallel to the proximal and distal base faces and the distal base face of the body portion including a first sizing indicator, wherein the sliding movement of the posterior portion indicates varying sizes on the first sizing indicator, said posterior portion including first and second skids extending in the proximal direction from the body portion, paid skids having anterior faces adapted to contact the posterior femoral condyles;

said body portion of said jig further including an aperture through its distal and proximal faces for receiving a bushing;

a bushing extending through said distal face and adapted to receive an intramedullary rod, said bushing further including a valgus angle guide means adapted to adjust the angular position of said intramedullary rod within the range of 15 degrees below and 15 degrees above an angle of ninety degrees with the distal face of the body portion of the jig;

a stylus removably attachable to the anterior face of said body portion, said stylus including a cross bar slideably engaged with the stylus for movement in the proximal-distal direction and a second sizing indicator, wherein the sliding movement of the cross bar indicates varying sizes on the second sizing indicator; and a distal cutting guise removably attachable to the anterior face of said body portion, said distal cutting guide having a plurality of fixation holes and a slot for guiding a saw blade for making the distal cut for resection of the distal femur, wherein the stylus and the distal cutting guide are both attachable to the anterior face but not simultaneously.

2. The set of instruments of claim 1 further comprising a spacer adapted to fit on the anterior surface of one of said skids of said jig.

3. The set of instruments of claim 2, wherein said spacer is designed to be a appropriate thickness to compensate for three degrees of external rotation.

4. The set of instruments of claim 3, wherein the spacer is approximately 0.1 inch in thickness.

5. The set of instruments of claim 1 wherein the body portion includes an anterior slot for making the anterior cut, the set further comprising a pin holder alignment guide, said pin holder alignment guide adapted to fit on said femur after the anterior and distal cuts are made and the jig is removed.

6. The set of instruments of claim 5, wherein said pin holder alignment guide includes distal face and a plurality of pairs of apertures through said distal face, each said pair of apertures corresponding to a femoral prosthesis size.

7. The set of instruments of claim 1 further including a chamfer cutting guide for guiding a saw blade, said chamfer cutting guide comprising a substantially rectangular block having a flat top surface adapted for placement against a flat-cut distal face of a femur resulting from the distal cut and a flat bottom surface, and connected by a posterior end for placement adjacent to the posterior condyles of a femur, said chamfer cutting guide including:

a first elongated rectangular aperture adapted for receiving a saw blade to make said first angle cut, said first elongated rectangular aperture extending through the chamfer cutting guide from the top surface to the bottom surface along a first plane and forming a first acute angle with the flat top surface; and a second elongated rectangular aperture adapted for receiving a saw blade to make said second angle cut, said second elongated rectangular aperture extending through the chamfer cutting guide from the top surface to the bottom surface along a second plane and forming a second acute angle with the flat top surface, wherein said second plane intersects said first plane;

a third elongated rectangular aperture adapted for receiving a saw blade, said third elongated rectangular aperture extending through said cutting guide from said top surface to said bottom surface and located adjacent to the posterior end of said cutting guide.

8. The set of instruments of claim 1 further including a chamfer cutting guide for guiding a saw blade, said guide comprising a substantially L-shaped block formed by intersecting distal and anterior portions, the distal portion having a flat top surface adapted for placement against a flat-cut distal face of a femur resulting from the distal cut and the anterior portion having a flat posterior surface adapted for placement against a flat-cut anterior face of a distal femur resulting from the anterior cut, said chamfer cutting guide including;

a first elongated rectangular aperture adapted for receiving a saw blade, said first elongated rectangular aperture extending through the distal portion of the chamfer cutting guide from the top surface to a bottom surface along a first plane and forming a first acute angle with the top surface of the distal portion;

a second elongated rectangular aperture adapted for receiving a saw blade, said second elongated rectangular aperture extending through the anterior portion of the chamfer cutting guide from an anterior surface to the posterior surface and forming a second acute angle with the flat posterior surface, wherein the first elongated rectangular aperture and the second elongated rectangular aperture each extend in the first plane so as to permit a straight saw blade to pass through both first and second apertures simultaneously;

a third elongated rectangular aperture adapted for receiving a saw blade, said third elongated rectangular aperture extending through the distal portion of the chamfer cutting guide from the top surface to the bottom surface along a second plane and forming a third acute angle with the flat top surface, wherein the second plane intersects the first plane; and a fourth elongated rectangular aperture adapted for receiving a saw blade, said fourth elongated rectangular aperture extending through said distal portion from the top surface to the bottom surface and located adjacent to a posterior end of said third elongated rectangular aperture.

9. The set of instruments of claim 1 further comprising posterior revision spacers and distal revision spacers, said posterior revision spacers adapted to fit on the anterior surface of said skids to contact the posterior femur, and said distal revision spacers adapted to fit onto the proximal face of said jig to contact the distal femur.

10. The spacers of claim 9, in which said revision spacers are each approximately nine millimeters in thickness.

11. A method for preparing the distal end of a femur for the implantation of a femoral prothesis comprising the steps of:

drilling a hole in the intramedullary canal of a femur; providing;

a jig comprising a body portion having parallel distal and proximal base faces, connected by parallel posterior and anterior base faces, wherein the proximal base face is adapted to abut the distal end of the femur;

said jig further including a posterior portion slideably engaged with said body portion for movement parallel to the proximal and distal base faces and the distal base face of the body portion including a first sizing indicator, wherein the sliding movement of the posterior portion indicates varying sizes on the first sizing indicator, said posterior portion including first and second skids extending in the proximal direction from the body portion, said skids having anterior faces adapted to contact the posterior femoral condyles;

said body portion of said jig further including an aperture through its distal and proximal faces for receiving a bushing;

a bushing extending through said distal face and adapted to receive an intramedullary rod, said bushing further including a valgus angle guide means adapted to adjust the angular position of said intramedullary rod within the range of 15 degrees below and 15 degrees above an angle of ninety degrees with the distal face of the body portion the jig;

a stylus removably attachable to the anterior face of said body portion, said stylus including a cross bar slidably engaged with the stylus for movement in the proximal-distal direction and a second sizing indicator, wherein the sliding movement of the cross bar indicates varying sizes on the second sizing indicator; and a distal cutting guide removably attachable to the anterior face of said body portion, said distal cutting guide having a plurality of fixation holes and a slot for guiding a saw blade for making the distal cut for resection of the distal femur, wherein the stylus and the distal cutting guide are both attachable to the anterior face but not simultaneously;

setting the valgus angle guide to the desired valgus angle;

attaching the stylus to the anterior surface of the jig;

flexing a knee to greater than 90°;

inserting the intramedullary rod through the bushing and into the femur;

placing the skids against the posterior condyles of femur;

positioning the jig against the uncut distal femoral condyle;

noting the size indicated on the first sizing indicator;

positioning the stylus so that the second sizing indicator indicates the same size as the first sizing indicator on the dictal face of the jig;

fixing the jig to the bone by inserting at least one pin through apertures extending through the proximal face of the body portion;

removing said stylus from the jig;

making an anterior cut so as to resect a portion of bone from the anterior distal femur;

attaching the distal cutting block to the anterior face of said body portion;

placing fixation pine through predetermined holes of said block and into the femur;

removing the jig;

assessing the implant size; and making a distal out using the slot provided on the distal cutting block so as to resect a portion of bone from the distal face of the femur to form a flat-cut surface.

12. The method of claim 11 further comprising the steps of removing the distal cutting block; placing a pin locator block having at least one pin aperture therethrough, against the distal femur; drilling at least one hole in said distal femur corresponding to at least one of said pin apertures; removing the pin locator block; placing a posterior chamfer cutting guide having a top surface against the flat-cut surface of the distal femur, said chamfer cutting guide having a posterior elongated rectangular aperture adapted to receive a saw blade and at least one extending pin portion; fixing the block to the femur by inserting the at least one extending pin portion into one of the drilled holes in the distal femur; and making a posterior cut using the elongated rectangular aperture as a guide so as to resect a portion of bone from the posterior condyles.

13. The method of claim 12 wherein said posterior chamfer cutting guide further includes second and third elongated rectangular apertures adapted to receive a saw blade; said second rectangular aperture extending through the cutting guide and forming a first acute angle with the top surface along a first plane and said third elongated rectangular aperture forming a second acute angle with the top surface along a second plane, wherein said second plane intersects said first plane, the method further comprising the steps of making two chamfer cuts to resect portions of bone using the second and third elongated rectangular apertures to guide a saw blade.

14. The method of claim 11 further comprising providing a chamfer cutting guide for guiding a saw blade, said guide comprising a substantially L-shaped block formed by intersecting distal and anterior portions, the distal portion having a flat top surface adapted for placement against a flat-cut distal face of a femur resulting from the distal cut and the anterior portion having a flat posterior surface adapted for placement against a flat-cut anterior face of a distal femur resulting from the anterior cut, said chamfer cutting guide including, a first elongated rectangular aperture adapted for receiving a saw blade, said first elongated rectangular aperture extending through the distal portion of the chamfer cutting guide from the top surface to a bottom surface along a first plane and forming a first acute angle with the top surface of the distal portion;

a second elongated rectangular aperture adapted for receiving a saw blade, said second elongated rectangular aperture extending through the anterior portion of the chamfer cutting guide from an anterior surface to the posterior surface and forming a second acute angle with the flat posterior surface, wherein the first elongated rectangular aperture and the second elongated rectangular aperture each extend in the first plane so as to permit a straight saw blade to pass through both first and second apertures simultaneously;

a third elongated rectangular aperture adapted for receiving a saw blade, said third elongated rectangular aperture extending through the distal portion of the chamfer cutting guide from the top surface to the bottom surface along a second plane and forming a third acute angle with the flat top surface, wherein the second plane intersects the first plane; and a fourth elongated rectangular aperture adapted for receiving a saw blade, said fourth elongated rectangular aperture extending through said distal portion from the top surface to the bottom surface and located adjacent to a posterior end of said third elongated rectangular aperture;

said chamfer cutting guide including at least one pin aperture therethrough;

fixing said chamfer cutting guide to the femur by inserting at least one pin through the pin aperture and into the femur;

resecting a portion of bone from the posterior condyles by inserting a saw blade through the fourth elongated rectangular aperture;

resecting a portion of bone from the distal and anterior faces of the femur by inserting a saw blade through the first and second elongated apertures; and resecting a portion of bone from the distal and posterior faces of the femur by inserting a saw blade through the third elongated rectangular aperture.

* * * * *